(12) United States Patent
Bibette et al.

(10) Patent No.: US 10,073,086 B2
(45) Date of Patent: Sep. 11, 2018

(54) DEVICE AND METHOD FOR CARRYING OUT HAEMATOLOGICAL AND BIOCHEMICAL MEASUREMENTS FROM A BIOLOGICAL SAMPLE

(71) Applicant: HORIBA ABX SAS, Montpellier (FR)

(72) Inventors: Jèrôme Bibette, Paris (FR); Philippe Nerin, Montpellier (FR); Jean-Philippe Gineys, Roquedur (FR); Gilles Cauet, Fontanès (FR)

(73) Assignee: HORIBA ABX SAS, Montpellier (FR)

( * ) Notice: Subject to any disclaimer, the term of this patent is extended or adjusted under 35 U.S.C. 154(b) by 50 days.

(21) Appl. No.: 14/376,270

(22) PCT Filed: Jan. 29, 2013

(86) PCT No.: PCT/EP2013/051619
§ 371 (c)(1),
(2) Date: Aug. 1, 2014

(87) PCT Pub. No.: WO2013/113670
PCT Pub. Date: Aug. 8, 2013

(65) Prior Publication Data
US 2014/0377771 A1    Dec. 25, 2014

(30) Foreign Application Priority Data

Feb. 2, 2012    (FR) ..................... 12 50961

(51) Int. Cl.
*G01N 33/49*    (2006.01)
*G01N 33/50*    (2006.01)
(Continued)

(52) U.S. Cl.
CPC ........... *G01N 33/5094* (2013.01); *G01N 1/38* (2013.01); *G01N 35/0098* (2013.01);
(Continued)

(58) Field of Classification Search
None
See application file for complete search history.

(56) References Cited

U.S. PATENT DOCUMENTS 4,030,888 A    6/1977    Yamamoto et al.
5,183,638 A    2/1993    Wakatake
(Continued)

FOREIGN PATENT DOCUMENTS

CN    1057339 A    12/1991
EP    0 409 606 A2    1/1991
(Continued)

*Primary Examiner* — Erik B Crawford
(74) *Attorney, Agent, or Firm* — Arent Fox LLP (57) ABSTRACT

The present invention concerns a device for analyzing biological parameters from a sample (6) comprising (i) first transferring means (5, 20, 25), (ii) first preparing means (7), (iii) means for measuring cellular components (8), (iv) second preparing means (10, 11, 22, 23, 24) capable of carrying out, on a sample from the first preparing means (7), at least one dilution with an assay reagent (R3) comprising particles functionalized at the surface with at least one ligand specific to at least one analyte of interest, (v) immunodetection measurement means (30, 31) capable of assaying at least one analyte of interest by measuring the aggregation of functionalized particles, said device further comprising (i) second transferring means (4, 21, 22, 26) at least partially separate from the first transferring means (5, 20, 25) and (ii) means for applying a magnetic field (28) capable of causing, by magnetic interaction, an acceleration of the aggregation of said functionalized particles, which comprise magnetic colloidal particles. The invention also concerns a method implemented in said device.

17 Claims, 4 Drawing Sheets (51) Int. Cl.
*G01N 1/38* (2006.01)
*G01N 35/00* (2006.01)
*G01N 35/10* (2006.01)
G01N 21/82 (2006.01)
G01N 15/14 (2006.01)

(52) U.S. Cl.
CPC ..... *G01N 35/10* (2013.01); *G01N 2015/1486* (2013.01); *G01N 2021/825* (2013.01); *G01N 2333/46* (2013.01); *G01N 2333/4737* (2013.01)

(56) References Cited

U.S. PATENT DOCUMENTS

| | | | |
|---|---|---|---|
| 5,215,714 A | | 6/1993 | Okada et al. |
| 5,290,708 A | | 3/1994 | Ashihara et al. |
| 5,939,326 A | | 8/1999 | Chupp et al. |
| 6,106,778 A | | 8/2000 | Oku et al. |
| 6,159,740 A | * | 12/2000 | Hudson ............ G01N 1/28 435/287.2 |
| 2004/0018629 A1 | * | 1/2004 | Kawate ............ G01N 15/1468 436/63 |
| 2005/0048673 A1 | | 3/2005 | Baudry et al. |
| 2007/0297279 A1 | * | 12/2007 | Gao ............ B01F 13/1055 366/160.4 |
| 2009/0117620 A1 | | 5/2009 | Fritchie et al. |
| 2010/0062518 A1 | * | 3/2010 | Banerjee ............ C12N 15/1003 435/270 |
| 2011/0053169 A1 | * | 3/2011 | Macioszek ............ C12Q 1/6851 435/6.11 |
| 2012/0142026 A1 | * | 6/2012 | Miller ............ B01L 3/50273 435/7.9 |
| 2012/0214175 A1 | * | 8/2012 | Graham ............ G01N 33/54326 435/7.25 |
| 2013/0078624 A1 | * | 3/2013 | Holmes ............ C12Q 1/00 435/6.11 |

FOREIGN PATENT DOCUMENTS

| | | |
|---|---|---|
| EP | 1 446 666 B1 | 5/2009 |
| JP | H02-502573 A | 8/1990 |
| JP | 03-051762 A | 3/1991 |
| JP | H04-218775 A | 8/1992 |
| JP | 05240859 A * | 9/1993 |
| JP | 2005-517899 A | 6/2005 |
| JP | 2011-503544 A | 1/2011 |
| WO | WO 88/07199 A1 | 9/1988 |
| WO | WO 02/37078 A2 | 5/2002 |
| WO | WO 03/044532 A1 | 5/2003 |

\* cited by examiner

DEVICE AND METHOD FOR CARRYING OUT HAEMATOLOGICAL AND BIOCHEMICAL MEASUREMENTS FROM A BIOLOGICAL SAMPLE

CROSS-REFERENCE TO RELATED APPLICATIONS

This application is the U.S. National Phase of International Patent Application No. PCT/EP2013/051619, filed Jan. 29, 2013, which claims priority to FR 1250961, filed Feb. 2, 2012, the contents of each are hereby incorporated by reference in their entireties.

TECHNICAL FIELD

The present invention relates to an analytical device and method for carrying out biological measurements, in particular hematological and biochemical measurements, using a biological sample, in particular a whole blood sample.

The field of the invention is more particularly, but in a nonlimiting manner, that of analysis systems.

PRIOR ART

The differentiation and counting of blood cell components, with in addition the assaying of at least one blood analyte, are of considerable interest in the diagnostic field. Indeed, most requests for biological analyses concern a complete blood count (CBC) with an additional request for the assaying of one or more analytes such as C-reactive protein (CRP) or else procalcitonin (PCT).

At the current time, these analyses require two samples to be taken: a first sample taken on an anticoagulant, intended for the hematological analysis, and a second sample taken without anticoagulant, intended for the biochemical analysis.

The sample intended for the biochemical analysis is centrifuged before being treated in the analyzers for assaying a serum or plasma biomolecule. The sample intended for the hematological analysis is stirred in order to keep the cells in suspension in the tube, before being treated using automated hematology devices. Furthermore, and quite often, the two samples taken are intended for distinct pieces of equipment located in different laboratories. This process is generally lengthy and expensive. As it happens, a number of situations require rapid measurement of the complete blood count and the assaying of one or more analytes. This approach can be envisioned provided that the technology enables assaying of whole blood (i.e. plasma with the blood cells). While this rapidity is unquestionably beneficial to the patient, it also contributes to reducing the delays and the costs of treatment.

For example, this type of analysis is required in ambulatory medicine, in emergency medicine or else in routine laboratories where the rate of analysis is a determining factor. In all these situations, it is sought to simplify the "pre-analytical" operations required for the preparation of the sample before the analysis, and very fast analysis is sought, with high levels of accuracy and reproducibility so as to enable a reliable diagnosis.

The combining of a hematological measurement and a biological assay is, for example, described in document U.S. Pat. No. 6,106,778 by Oku et al. Said document describes an analytical device comprising a hematology module and a biochemistry module, and allowing the measurement of the following hematological parameters: white blood cell count (WBC count), red blood cell count (RBC count), platelet count (PLT count), mean corpuscular volume (MCV), hematocrit (Hct) and hemoglobin (Hgb).

A major drawback of this device is that it does not allow high analysis rates. This is because a single carriage and a single sampling needle are used to sample and distribute the blood and the reagents in the hematology module and the biochemistry module. It follows that the occupation rate of the needle is too high to allow hematological analysis times shorter, for example, than 60 seconds.

Another drawback comes from the fact that the same needle is used to store the blood sample and the reagents before the hemodilution step, which poses a problem of contamination (carry over) detrimental to sensitive assays for low-abundance analytes.

Finally, the biological assay as described in said document does not make it possible to achieve an immunological reaction speed for assaying the analyte being sought which is compatible with high analysis rates while at the same time conferring a sensitive, reproducible measurement without inter-sample contamination. It is based on a well-known principle which makes use of colloidal aggregation phenomena. This test, often referred to as "LAI" for "latex agglutination immunoassay", is based on the following principle: antibodies specific for a given antigen are grafted onto colloidal particles, and the capture of the antigen by at least two particles thus results in an aggregate which modifies the turbidity of the solution, thereby allowing a quantitative assay of the antigens.

The speed of this aggregation reaction of course partly depends on the antigen concentration. When seeking the best sensitivity, the particle concentration must always exceed the antigen concentration. In particular, a particle concentration which is about ten times the antigen concentration gives the best compromise, in the knowledge that, if the number of doublets expected (set by the number of antigens) is very minor, compared with the number of singlets (non-aggregated particles), the signal-to-noise ratio is affected.

The speed of the colloidal aggregation reaction is also linked to the diffusion coefficients of the particles (translation and rotation) and to the surface concentration of antibodies grafted onto the surface of the colloidal particles. It is also accepted that this reaction speed sets, for a given incubation time, the sensitivity and the detection threshold of the test. Thus, a shorter incubation time will be required, for an equal sensitivity, a faster aggregation speed.

Several approaches have been proposed for accelerating this reaction without significantly increasing the nonspecific noise, and thus offering either a greater sensitivity, or a higher assay rate, by reducing the incubation time. These methods all have in common the fact that they increase the frequency of collision of particles by creating a local increase, during the application of an external field, in the concentration of colloidal particles.

Three distinct approaches are known at the current time: the use of stationary ultrasonic waves, the use of alternating electric fields in macroscopic two-dimensional or three-dimensional systems and, finally, the use of magnetic fields combined with superparamagnetic colloidal particles. In the case of stationary ultrasonic waves, local enrichment of particles occurs in the high acoustic pressure zones; in the case of confined two-dimensional systems with the application of a high-frequency alternating electric field in the perpendicular direction, the local enrichment occurs via the existence of attractive forces of hydrodynamic origin (induced by ion circulation); in the case of macroscopic systems with the application of a high-frequency alternating electric field, the local enrichment occurs in the form of chains of particles under the action of dipolar colloidal forces (induced by the difference in polarizability); in the case of macroscopic systems with superparamagnetic colloidal particles subjected to a uniform magnetic field, the enrichment occurs in the form of chains induced by magnetic dipolar interactions.

Document EP 1 446 666 by Bibette et al. is in particular known, said document describing a method for detecting analytes using colloidal magnetic particles, i.e. magnetic particles with a size of between 5 nanometers and 10 micrometers.

These particles are functionalized at their surface with a ligand which can be an antibody, an antigen or any other molecule capable of specifically binding the analyte to be assayed and incorporating a magnetic material capable of adopting a superparamagnetic behavior. Under the effect of the application of a magnetic field, they have a tendency to agglutinate as a chain, thus promoting the attachment of the analyte to two distinct particles. After the magnetic field is turned off, only the particles bound by the analyte remain organized in permanent chains. The measurement is carried out by means of an optical method, by microscopy or by means of a density measurement. The measurement examples described relate in particular to assays of analytes in a calibration plasma solution.

An objective of the present invention is to provide a device and a method for rapidly and reliably carrying out hematological and biochemical measurements using a whole blood sample, i.e. a sample in which the cells have not been removed beforehand.

Another objective of the present invention is to provide a device and a method for carrying out hematological and biochemical measurements using a single whole blood specimen in an automated manner.

Another objective of the present invention is to provide a device and a method for carrying out hematological and biochemical measurements at a high rate using whole blood samples, of the order, for example, of one measurement per minute.

Another objective of the present invention is to provide a device and a method for carrying out hematological and biochemical measurements using a whole blood sample which makes it possible to achieve high measurement sensitivity and dynamics for biochemical measurements.

Finally, an objective of the present invention is to provide a device and a method for carrying out hematological and biochemical measurements using a whole blood sample, in which the risks of cross contamination between the blood sample and the reagents are minimized.

DISCLOSURE OF THE INVENTION

This objective is achieved with a device for analyzing biological parameters using a biological sample, comprising:
first transferring means capable of at least partially transferring said biological sample to first preparing means,
first preparing means capable of carrying out at least one dilution of said biological sample with at least one diluent and/or one reagent,
second preparing means capable of carrying out, on a first sample from the first preparing means, at least one dilution with an assay reagent comprising particles functionalized at the surface with at least one ligand specific for at least one analyte of interest,
immunodetection measurement means capable of assaying, on a sample from the second preparing means, at least one analyte of interest by measuring the degree of aggregation of functionalized particles in a measuring cuvette, characterized in that it also comprises:
second transferring means at least partially separate from the first transferring means and capable of taking said first sample diluted beforehand in the first preparing means, and of transferring it to the second preparing means, and
means for applying a magnetic field in said measuring cuvette, capable of causing, by magnetic interaction, an acceleration of the aggregation of said functionalized particles, which comprise magnetic colloidal particles.

According to the embodiments, the device according to the invention may also comprise means for measuring a cell component which are capable of providing, from the biological sample, at least one measurement of cell volume relative to the total volume.

According to other embodiments, the device according to the invention may also comprise means for measuring a cell component which are capable of providing, from a second sample from the first preparing means, at least one measurement of cell volume relative to the total volume.

According to Embodiments:
the second preparing means may be capable of carrying out at least one lysis operation;
the first sample from the first preparing means may have undergone a lysis operation beforehand;
the lysis operation may be carried out with a lytic reagent, or by other means, such as a physical method;
the second transferring means may be partially or totally separate from the first transferring means. They may be capable of functioning simultaneously or in parallel with the first transferring means.

The functionalized particles may comprise:
particles comprising a ferromagnetic material;
particles which have a core with a high iron oxide content surrounded by a shell made of a polymer material;
particles having an essentially spherical shape with an average diameter of less than 1 micrometer, preferably less than 500 nanometers, and more preferably between 100 and 300 nanometers.

The immunodetection measurement means may comprise optical measurement means with at least one light source and at least one detector which are placed in proximity to the measuring cuvette, said cuvette having, at least at the level of said optical measurement means, substantially transparent walls.

The immunodetection measurement means may also comprise optical conditioning means capable of producing, from at least one light source, a collimated light beam which passes through the measuring cuvette.

The device according to the invention may comprise at least one light source capable of emitting in optical wavelengths of between 400 nanometers and 4 micrometers, and preferably between 600 nanometers and 900 nanometers.

According to embodiments, the device according to the invention may also comprise:
an electromagnet capable of producing a magnetic field in the measuring cuvette,
means for regulating the temperature of the measuring cuvette, and/or means for measuring the temperature of the measuring cuvette, a storage container regulated at an optimum temperature for storing the assay reagent, it being possible for said temperature to preferably be between 5° C. and 15° C., and agitating means for placing and/or keeping the functionalized particles in suspension in the stored assay reagent, it being possible for said means to be via ultrasound and to comprise at least one of the following means: an external sonotrode coupled to the storage container, a sonotrode immersed in the assay reagent.

According to embodiments, the first transferring means may comprise a sampling needle and means for moving said sampling needle.

According to embodiments, the second transferring means may comprise:

a sampling needle and means for moving said sampling needle which are capable of transferring assay reagent into the measuring cuvette, a sampling valve capable of taking a sample from the first preparing means.

The biological sample may comprise any type of appropriate biological sample, for instance a bone marrow sample, a cerebrospinal fluid sample, a lymph sample, a urine sample, or a whole blood sample, etc.

Thus, according to particular embodiments, the device according to the invention may be a device for analyzing biological parameters using a biological sample comprising a whole blood sample.

It may also comprise means for measuring a cell component which are capable of providing at least one hematocrit measurement.

According to embodiments, this hematocrit measurement may be provided:

from the biological sample, from a second sample from the first preparing means.

More generally, the means for measuring a cell component may comprise hematocrit measurement means, or hematology measurement means capable of providing at least one hematology measurement among a blood element differentiation and/or count, an assay of hemoglobin, a hematocrit measurement and a cell volume measurement.

According to another aspect of the invention, a method for analyzing biological parameters using a biological sample is provided, comprising steps of:

transferring, via first transferring means, at least one part of said biological sample to first preparing means, carrying out, via first preparing means, at least one dilution of said biological sample with at least one diluent and/or one reagent, carrying out, via second preparing means, on a first sample from the first preparing means, at least one dilution with an assay reagent comprising particles functionalized at the surface with at least one ligand specific for at least one analyte of interest, assaying, via immunodetection measurement means, at least one analyte of interest with a sample from the second preparing means, by measuring, in a measuring cuvette, the degree of aggregation of functionalized particles, characterized in that it also comprises steps of:

taking, via second transferring means, at least partially separate from the first transferring means, said first sample diluted beforehand in the first preparing means, and transferring to the second preparing means, and applying a magnetic field in said measuring cuvette so as to cause, by magnetic interaction, an acceleration of the aggregation of said functionalized particles, which comprise magnetic colloidal particles.

The method according to the invention may also comprise a step of lysis of the sample prior to the assaying of the analyte of interest. It may in particular comprise a step of carrying out, via the second preparing means, on the first sample from the first preparing means, at least one lysis operation. This lysis operation can be carried out with a lytic reagent.

According to embodiments, the method according to the invention may also comprise a step of obtaining, via means for measuring a cell component, from the biological sample, at least one measurement of cell volume relative to the total volume.

According to other embodiments, the method according to the invention may also comprise a step of obtaining, via means for measuring a cell component, from a second sample from the first preparing means, at least one measurement of cell volume relative to the total volume.

The assaying of at least one analyte of interest may comprise steps of:

introducing into the measuring cuvette a measuring solution comprising at least one sample and assay reagent, measuring a first optical intensity through the measuring cuvette, applying a magnetic field in the measuring cuvette for a given period of time, so as to allow the aggregation of the functionalized particles under the effect of the magnetic field, after the magnetic field has been turned off, measuring a second optical intensity representative of the residual aggregation of the functionalized particles due to the couplings between ligand and analyte of interest, calculating a variation in optical density as a function of the ratio of said first and second optical intensities, and applying a calibration function determined beforehand so as to calculate the concentration of the protein of interest from the variation in optical density.

According to embodiments, the biological sample may be diluted to a degree greater than ×500 in the measuring solution.

According to embodiments, the method according to the invention may be a method for analyzing biological parameters using a biological sample which comprises a whole blood sample.

It may use, for assaying the analyte of interest:

a lytic reagent comprising saponin, a buffer solution capable of maintaining an optimal pH.

According to embodiments:

the analyte of interest may be a protein of interest, the method according to the invention may use particles functionalized with a ligand capable of enabling C-reactive protein (CRP) to be assayed.

Advantageously, the use of colloidal particles with superparamagnetic properties and of a uniform magnetic field allows good control and excellent performance levels in terms of reaction kinetics. The main reason is linked to the origin of the forces involved: the superparamagnetic nature (relative susceptibility of the order of 1) of the colloids makes it possible to apply forces of the order of a few tens of piconewtons on colloids approximately 200 nm in diameter, without blocking the rotational diffusivity. Intimate contact between particles in the chain can be established while at the same time leaving the particles subjected to the action of rotational Brownian motion, and the neighboring particles having captured an antigen (or an analyte or a protein of interest) can rapidly find the orientation conducive to forming doublets. Thus, in a few seconds, an antigen or a protein of interest can be assayed with a sensitivity of the order of one picomole per liter.

It is recalled that the superparamagnetic properties are reflected by the fact that the magnetization of the particles appears to be zero in the absence of a magnetic field, but that said particles exhibit a high magnetic susceptibility in the presence of this field. They are naturally dispersed in the absence of a magnetic field and they group together in the form of chains in the presence of the latter.

The efficiency and the rapidity of the aggregation reaction make it possible to obtain measurement rates that are higher than the prior art devices since the recognition between an antibody (or a ligand) and an antigen (or an analyte or a protein of interest) is in this case forced by the magnetic field and not left to the chance encounter that would result from the random impact of the particles initiated by Brownian motion. This encounter forced by the magnetic field makes it possible to rapidly form aggregates and thus, in a given time, to considerably increase the sensitivity of a biological test.

This efficiency also makes it possible to use high degrees of dilution (greater than ×500, or even ×1000 or ×1500) while at the same time retaining reasonable measuring times.

In the field of blood analyses in particular, the possibility of using high degrees of dilution for assaying analytes of interest or proteins on whole blood is a particularly advantageous aspect of the invention. In the prior art devices which use a method of aggregation of latex particles by simple agitation, such as, for example, that described in U.S. Pat. No. 6,106,778, owing to the slow reaction kinetics, the degree of dilution used is instead of the order of ×15 to ×51 (for example for Micros CRP200®). As it happens, the blood medium with hemoglobin is very absorbent in visible wavelengths. This means that optical measurements have to be made in the infrared range, and because of the long wavelengths, these measurements are simple measurements of absorption or optical density that are influenced by all the effects of absorption and of turbidity of the medium.

With degrees of dilution of the order of ×500 or more, the medium analyzed is much less absorbent with respect to visible wavelengths. This makes it possible to use shorter wavelengths and to obtain a measurement in which the losses due to the phenomenon of scattering on the particle aggregates are significant relative to the absorption of the medium. The optical measurement thus becomes much more (or more closely) representative of the phenomenon sought and makes it possible to obtain very high sensitivity ranges and a measurement noise level which is lower than the simple absorption measurements of the prior art.

In addition, the iron oxide used for the colloidal particles has proportions of absorption as a function of optical wavelength that are close to those of hemoglobin. Just as for hemoglobin, there are transparency wavelengths located between 600 and 900 nm where the measurement can be carried out without too much hindrance with respect to the absorption properties of the medium. Thus, the nonaggregated particles cause little disruption of the spectroscopic properties of the medium and therefore the measurement. The matrix effect, i.e. the influence of the medium on the elements to be assayed, is reduced.

By way of example, the device according to the invention makes it possible to assay C-reactive protein (CRP) in the range 2-200 mg/l using a degree of dilution of the order of ×1500.

According to another advantageous aspect of the invention, the sampling needle which is used to transfer the assay reagent into the measuring cuvette is never in contact with the undiluted whole blood sample. This represents a real advantage compared with the prior art, since this arrangement makes it possible, on the one hand, to limit the pollution of the assay reagent by the blood sample itself, and, on the other hand, to reduce the carry over interference effect from one sample to the other on the final dilution.

According to likewise an advantageous aspect, the cell component measurements (or hematology measurements) and immunodetection measurements are carried out in parallel, and make it possible to obtain high measurement rates, of the order of one minute for a blood sample.

In addition, the coupling of the hematology and immunodetection measurements is not limited to the fluidic part or to the sampling. Indeed, the immunodetection measurements require calibrations which can advantageously exploit parameters resulting from the hematology measurements.

For example, the hematocrit value can be used to express the concentration of the analyte (initially assayed on whole blood) in the serum fraction of the sample: in this case, the concentration of the analyte assayed is divided by the hematocrit value, which is the sum of the leukocrit, the thrombocrit and the erythrocrit. It is also possible to divide the value obtained on whole blood by a polynomial of degree greater than or equal to 2 so as to take into account nonlinear effects introduced by the measuring device.

According to another example, the differential cell count can be taken into account for detecting certain abnormalities which are interference sources, such as an excessively high number of red blood cells and/or of white blood cells and/or of platelets. In this case, the result of the analyte assay is not displayed.

These count measurements can also be taken into account for correcting the measurement of optical density obtained during the assay measurements, for example by applying a polynomial correction relationship such as:

$$OD = OD^\circ - \sum_i ai(RBC\#) \wedge i - \sum_j bi(WBC\#) \wedge j - \sum_k ci(PLT\#) \wedge k$$

where:
i, j and k are integers;
RBC#, WBC# and PLT# are the red blood cell, white blood cell and platelet counts expressed per unit of volume (L);
ai, bi and ci are coefficients;
OD° is the value of the optical density as measured, not corrected and comprising measurement artifacts linked to an excess of cells or corresponding debris in the reaction medium;
OD is the value of the optical density corrected on the basis of the data resulting from the hematology measurements.

This relationship is not limiting; it can in particular involve other parameters, such as the cell volumetry.

DESCRIPTION OF THE FIGURES AND EMBODIMENTS

Other advantages and particularities of the invention will become apparent on reading the detailed description of uses and of embodiments which are in no way limiting, and of the following appended drawings.

Figure 1:
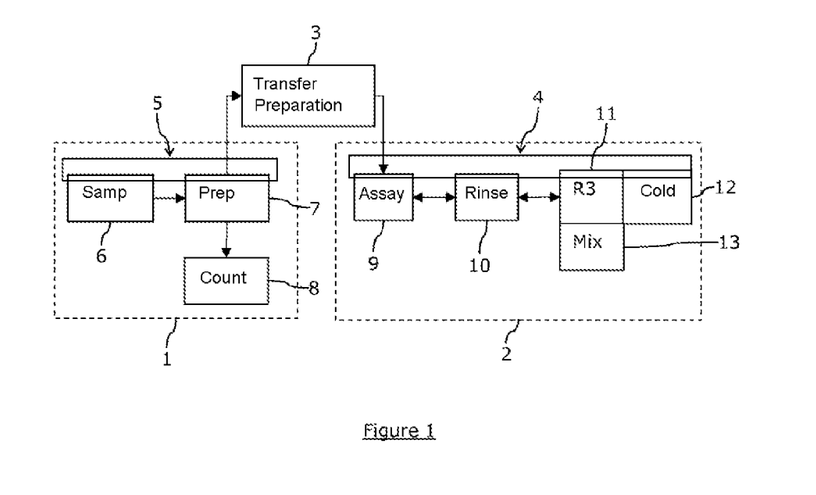
FIG. 1 presents a functional diagram of a device according to the invention, according to a first embodiment.
Figure 2:
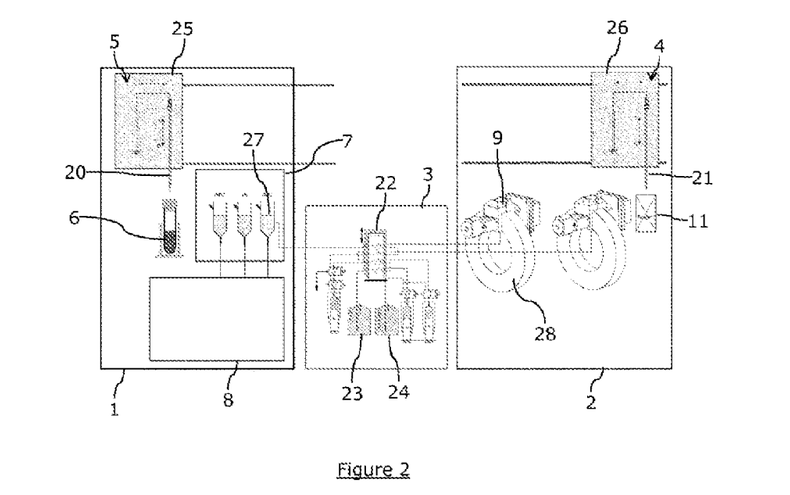
FIG. 2 presents a diagrammatic representation of a device according to the invention, according to a first embodiment.

With reference to FIGS. 1 and 2, a first embodiment of an analytical device which makes it possible to obtain a hemogram from a single whole blood sample 6, and the assaying of at least one blood analyte, will be described. This device is designed so as to make it possible to achieve a high analysis rate, of the order of at least one complete analysis per minute.

This device is composed of a hematology module 1 and an immunodetection module 2. These two modules are coupled by means of a mechanical and fluidic interface, the transferring module 3, which allows them to use one and the same blood sample 6. They operate in parallel. This representation in the form of modules is of course purely functional, in order to facilitate understanding, and it is in no way limiting with regard to the physical implementation of the components.

The hematology module 1 is based on principles and technologies known to those skilled in the art, for instance those described in U.S. Pat. No. 6,106,778. This module 1 is therefore described here in a relatively succinct manner. It is composed mainly of three subassemblies which are the first sampling and transferring means 5, the first preparing means 7 and the hematology measurement means 8.

The device may comprise a sample changer which makes it possible to automatically introduce a blood sample contained in a tube 6.

The first sampling and transferring means 5 comprise a hollow metal needle 20 connected to a moving and suctioning system, which makes it possible to take a whole blood sample from the sample tube 6.

The surface of this needle 20 is preferably treated with a treatment intended to limit the adhesion of the various cell and chemical compounds of the blood.

When the device is designed to operate with hermetically closed sample tubes 6, this needle 20 can be equipped with a system for piercing the stopper. In this case, the device also comprises a pressure equilibration system.

The needle 20 is coupled to a mobile carriage 25 which makes it possible to position it above the containers of the first preparing means 7 and to distribute the blood aliquots in the hematology module 1.

The first preparing means 7 comprise several mixture containers 27, each connected to one or more specific reagent feeds, a discharge outlet, a bubbling circuit for the mixtures and a circuit for transfer to the hematology measurement device 8. They enable mixing and precise assaying of the aliquot brought by the needle 20 with various reagents, so as to obtain the mixtures required for establishing the hemogram and for the counting.

Each container 27 is associated with one or more reagents for a specific treatment of the sample: dilution in a reagent with a tonicity equal to that of red blood cells, lysis of the red blood cells, lysis and formation of a stable complex of hemoglobin, etc. These mixtures are then analyzed by specific devices which comprise fluidic elements, known to those skilled in the art, for enabling a complete hemogram to be carried out at the desired rate. These dilution containers 27 and the hematology measurement device 8 thus allow counting and differentiation of leukocytes, erythrocytes and thrombocytes. These hematological data comprise other parameters, such as measurement of the hemocrit Hct or the Wintrobe indices. Finally, the leukocytes can be differentiated into cell subpopulations enabling the counting of lymphocytes, monocytes, granular leukocytes and/or immature cells.

The hematology measurement means 8 are based on known flow cytometry techniques. They comprise moving means for passing the blood cells, one by one, into one or more counters, and combine impedance measurements with optical measurements. The volume of mixture analyzed is controlled in such a way as to meet the accuracy requirements, in particular for the counts. The processing of these data makes it possible to obtain the hematological results.

The transferring module 3 provides the interface between the hematology module 1 and the immunodetection module 2. It allows the recovery of one or more aliquot(s) of blood in the hematology module 1 and the transfer thereof to the immunodetection module 2.

It also makes it possible to continue the preparation of the mixture for the immunological measurement, via additional dilutions and the addition of one or more reagents.

The transferring module 3 comprises second transferring means with a sampling valve 22 which makes it possible to take a sample in a cuvette 27 within the first preparing means 7. It also comprises a part of the second preparing means (23, 24) for preparing the samples for the immunodetection module 2. The operation thereof is explained in detail later on.

The immunodetection module 2 comprises a measuring cuvette 9. It also comprises another part of the second preparing means (10, 11, 12, and 13) with a set of reagents equipped with their means of distribution and a temperature-regulated compartment 11 for storing the assay reagent R3 containing the magnetic particles. It also comprises second transferring means 4 with a specific needle 21 mounted on a carriage 26 or on a motorized arm (not 15 represented). It also comprises a rinsing cuvette 10 for rinsing the needle 21.

The measuring cuvette 9 is equipped with a specific optic for carrying out a measurement of optical density in the medium, optionally corrected via a measurement of the power of the light source. It has an electromagnet 28 produced with a coil, which allows a magnetic field to be applied to the medium measured. The application of this field and its amplitude as a function of time define the magnetization cycle. It is controlled by an electronic device which allows the coercive field to be canceled if necessary, and it is synchronized with the optical density variation measurement. The profile of this cycle depends on the type of immunological measurement carried out. The measurement principle is explained in more detail precisely later on.

The measuring cuvette 9 is kept in a temperature-regulated atmosphere. It is equipped with a secondary heating system, for example with a heated aluminum block placed around this cuvette 9 in the available zones. A temperature probe makes it possible to measure its temperature, which may then be regulated if necessary.

Figure 3:
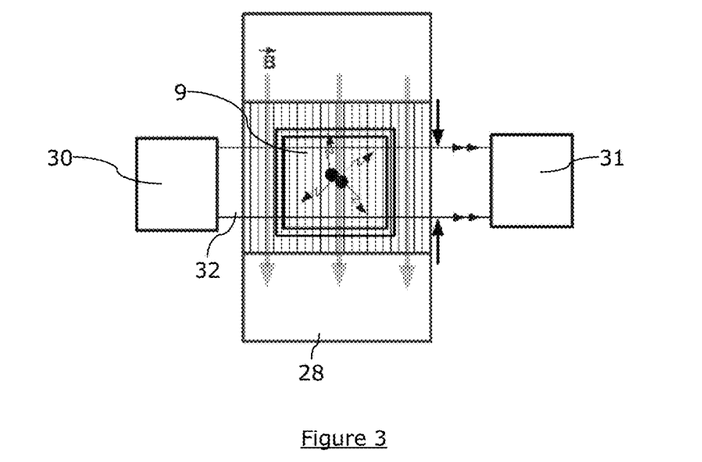
FIG. 3 presents a sectional view of the immunodetection measuring cuvette.

With reference to FIG. 3, this measuring cuvette 9 has a capacity of the order of a few hundred µl. It comprises two opposite transparent plane surfaces in the direction of passage of the light beam 32. Its volume is designed so as to maximize the volume illuminated. Preferentially, it may comprise a discharge funnel for efficient rinsing and drying. Depending on the applications, it may be made of various materials, such as glass, quartz or injection-molded or machined plastic, for instance PMMA or polyamide, etc. It preferably undergoes a physicochemical surface treatment in order to reduce the adhesion of the various cell and chemical compounds of the blood.

The temperature-regulated compartment 11 makes it possible to maintain the reagent R3 using the magnetic particles at a storage temperature of a free degrees (typically between 5 and 15° C.), which makes it possible to store it actually within the analyzer. It is equipped with an agitation system, for example an ultrasonic agitation system 13, which makes it possible to place and keep the colloidal particles in suspension in their solution, and also to dissociate any aggregates due to nonspecific interactions. This ultrasonic agitation system 13 comprises a sonotrode (i.e. a part which transmits ultrasound) external to the reagent bottle, and mechanically coupled to the latter. Other agitation systems known to those skilled in the art may of course be envisioned.

The reagents for controlling or calibrating the immunological measurement module 2 can also be stored in this temperature-regulated compartment 11.

A temperature regulation system 12 makes it possible to maintain the temperature of the compartment 11. It is not necessary to have great precision. The systems conventionally used in industry and known to those skilled in the art are largely sufficient. For example, it may be a Peltier-effect module controlled by an all-or-nothing regulation loop.

The specific sampling needle 21 is dedicated to the immunodetection module 2. This is necessary in order to be able to guarantee the cycle rate, the occupation rate of the needle 20 of the hematology module 1 being high in a high throughput analyzer. In the configuration presented here, it is associated with actuators and with a carriage 26 enabling its vertical and horizontal movement above the measuring cuvette 9, the bottle of magnetic particles 11 and the rinsing cuvette 10.

This sampling needle 21 is used for the sampling of the magnetic particles and the dispensing thereof into the solution analyzed, which limits the risks of contamination of the assay reagent R3. It can also be used for carrying out the mixing by successive suctioning and discharging of the mixture in the measuring cuvette 9.

The reagents used in the immunodetection module 2 perform three main functions, namely:
blood cell lysis,
maintaining a pH at a stable and defined value,
agglutination reaction.

R1 will be called the lytic reagent, R2 the buffer solution and R3 the assay reagent containing the magnetic particles.

The reagent R1 comprises a lytic agent which comprises a detergent or any other molecule having cell membrane modifying and fragmenting properties. It may comprise, for example, a detergent of the saponin class, or else of the quaternary ammonium class. It may also comprise an anionic detergent chosen from the bile acid class.

The buffer solution R2 comprises a buffer system capable of maintaining a constant pH during the progression of the reaction. This may be, for example, a 50 mM glycine buffer, with a pH of the order of 8.5.

The lytic reagent R1 and the buffer solution R2 can be combined in a single reagent.

The assay reagent R3 comprises submicrometric particles at the surface of which are grafted antibodies directed against the analyte to be assayed. These particles are characterized by a mean diameter D and a standard deviation $\sigma_D$ such that $\sigma_D/D<20\%$, the mean diameter being between 100 and 300 nm. These substantially spherically shaped particles are formed from a shell made of polymer material, the thickness of which is a few tens of nanometers, within which is a core with a high iron oxide content. Examples of such a reagent R3 can be found in EP 1 446 666.

The detection of the particulate aggregates is carried out by means of an optical device optimized for detecting the light scattered by the colloidal mixture. It comprises a light source 30 of the light-emitting diode (LED) type and a detector 31 with a photodiode or a photomultiplier placed on either side of the measuring cuvette 9. It also comprises beam conditioning means which make it possible to generate, through the cuvette 9, a collimated light beam 32, the divergence of which is minimal and ideally limited by the diffraction.

Generally, it is preferable to use a light source 30 which has a low temporal coherence, in order to reduce or avoid various optical noises, such as the laser granularity phenomenon or else multiple interferences in the analysis medium, resulting from multiple reflections on the walls of the assembly.

Figure 4:
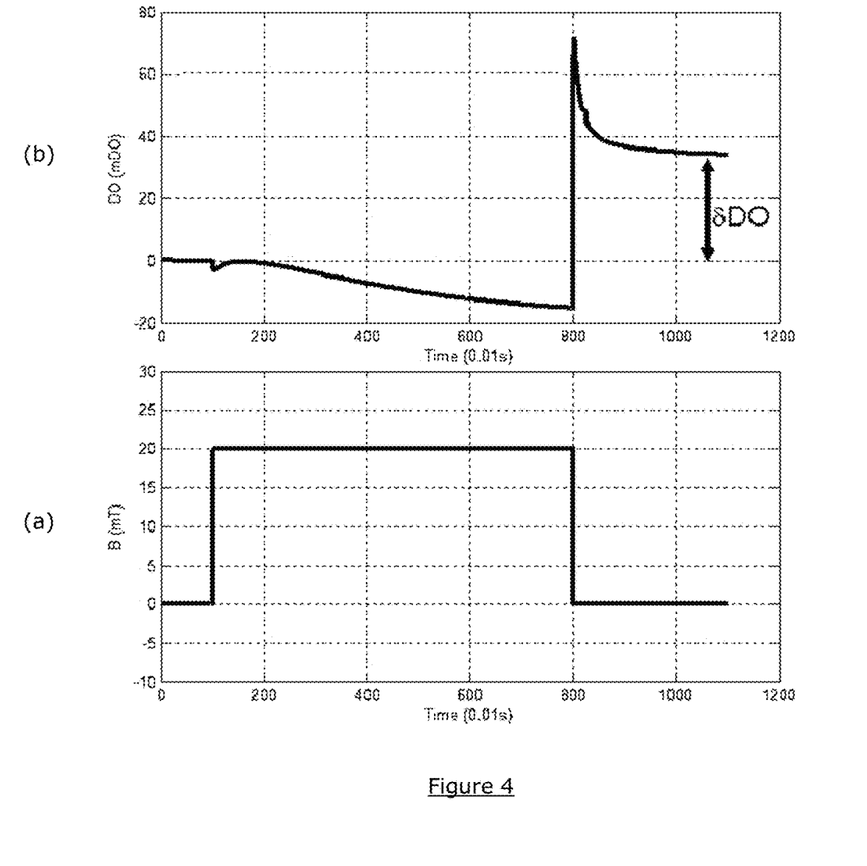
FIG. 4 presents an example of measurement signal acquisition during assay measurements, with, in FIG. 4(a), the magnetic field and, in FIG. 4(b), the optical signal.

With reference to FIG. 4, in order to carry out an assay measurement, a magnetization cycle is performed, which comprises the application of a magnetic field with a temporal profile which is defined in terms of its form, its duration, its number of periods, etc. In the example presented, this magnetization cycle comprises the application of a magnetic field temporal step function, as illustrated in FIG. 4(a). During the application of the magnetic field, the colloidal magnetic particles group together in chains. After interruption of the magnetic field, they are again dispersed, with the exception of the aggregates formed by the capturing of the analyte or of the protein of interest by the ligands or the antibodies.

The optical signal transmitted through the measuring cuvette 9 is recorded before, during and after the magnetization cycle, as illustrated in FIG. 4(b). A variation in the transmitted light is then determined before and after the application of the magnetic field by calculating a variation in optical density $\delta OD = -\log(It/Io)$ where "Log" is the logarithm operation, It is the intensity of the transmitted light after application of the magnetic field and Io is the intensity of the transmitted light before application of the magnetic field. This variation in transmitted light is due to the scattering by the aggregates which have formed.

For each analyte assayed, denoted i, of concentration $C_i$, the method makes it possible to determine a variation $\delta OD_i$. In practice, the $\delta OD_i$ quantity measured is not directly proportional to $C_i$. A mathematic function, which may be a polynomial, the coefficients of which are determined by calibration, makes it possible to determine $C_i$ by a relationship of the form $C_i = F_i(\delta OD_i)$, where $F_i$ is a function specific to the analyte $C_i$.

Figure 5:
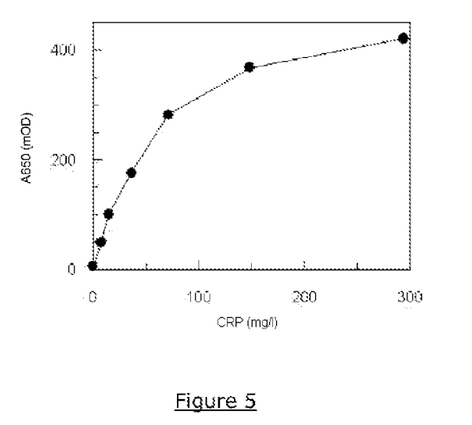
FIG. 5 presents an example of a calibration curve for assaying C-reactive protein in a whole blood sample.

FIG. 5 presents an example of a calibration function for assaying C-reactive protein in a whole blood sample.

An exemplary embodiment of the method according to the invention for assaying two different analytes will now be more precisely described.

The hematology module 1 is designed so as to be able to perform 80 tests per hour.

The duration of a cycle for obtaining the complete hemogram and also the blood element count is 45 seconds.

The immunodetection module 2 comprises two measuring cuvettes 9, which make it possible to carry out two simultaneous measurements, also in 45 seconds. These measurements may comprise measurements on two different analytes, or measurements on the same analyte over two different measurement ranges.

The transferring module 3 makes it possible to sample a dilution initially prepared by the hematology module 1 for the red blood cell count, through a sampling valve 22. It then simultaneously feeds the two measuring cuvettes 9, with two different preparations of the same blood sample.

The device executes the following temporal sequence:

The hematology module 1 samples the blood aliquot 6 and rinses its needle 20 from 0 to 10 s. In parallel, the various cuvettes of the two modules are rinsed. The hematology module 1 then prepares the first dilution for the red blood cell (RBC) count, while the immunodetection module 2 samples the assay reagents R3 and begins to dispense them into its two measuring cuvettes 9 (each cuvette receiving a different assay reagent R3, specific for a protein). After about twenty seconds, part of the RBC dilution is transferred to the immunodetection module 2, while the latter finishes the dispensing of the assay reagents R3. The hematology module 1 continues, in parallel, the preparation of the other mixtures in its other containers 27. It is now about 25 s from the beginning of the cycle and the hematology module finishes its cycle on its part up until 45 s. During this time, the solutions in the measuring cuvettes 9 of the immunodetection module 2 are mixed and then the assay measurement begins, and finishes at 45 s from the beginning of the cycle.

It should be noted that the assay measurement cycle lasts only 9 seconds, and the rate is consequently limited by the durations of the preparation cycle. The method according to the invention is therefore compatible with much higher measurement rates, using suitable preparation systems, for example based on microfluidic systems.

Figure 6:
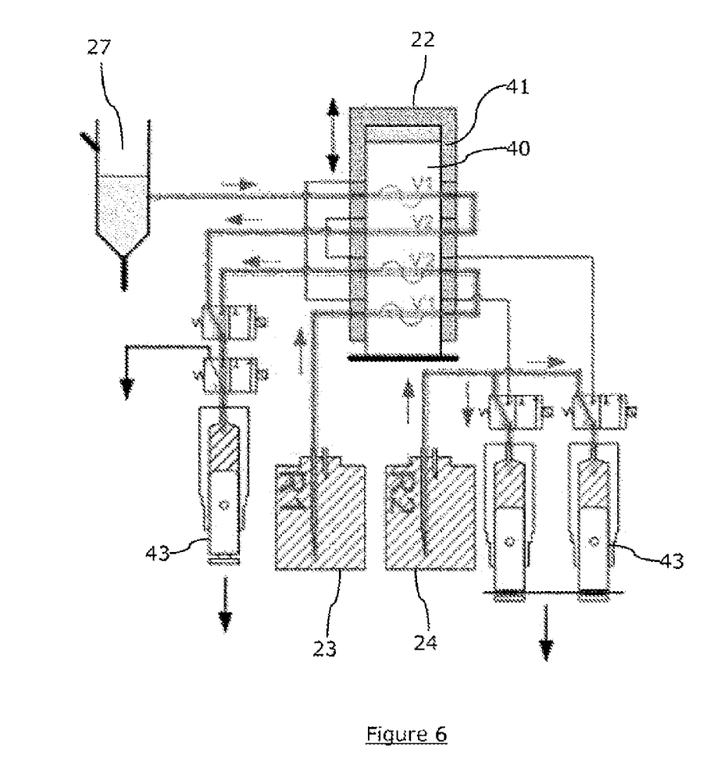
FIG. 6 illustrates the operation of the sampling valve, in a step of taking the sample and the reagents.
Figure 7:
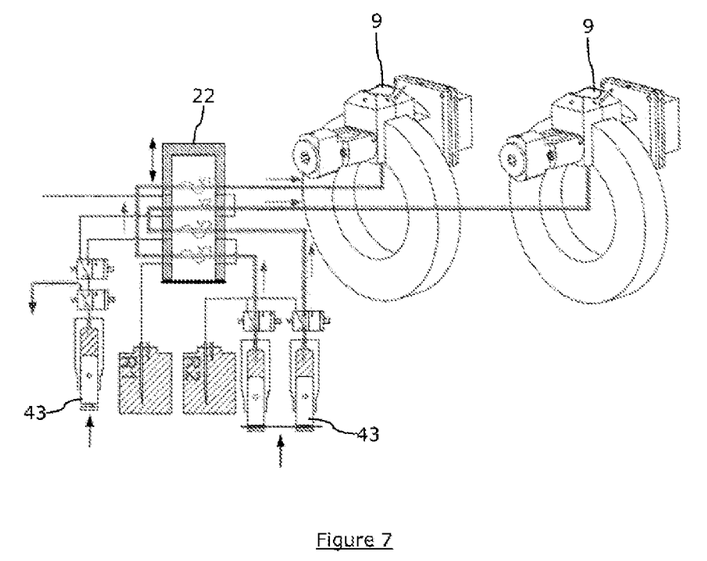
FIG. 7 illustrates the operation of the sampling valve in a step of transferring and mixing the sample with the reagents in the measuring cuvettes.

The sampling valve 22 used in this embodiment is a sampling valve of slide gate type, well known to those skilled in the art. It comprises a translationally mobile part 40 in a support 41. The mobile part 40 has capillary tubes passing through it which make it possible to store aliquots, and the support 41 comprises fluidic ports. An aliquot can be suctioned by a first fluidic port and stored in the mobile part 40, and then the mobile part 40 is moved such that the aliquot can be expelled via another fluidic port.

The sampling valve 22 manages two types of aliquots:
a first series of aliquots corresponding to the sampling of several predetermined volumes of a sample dilution contained within the hematology module: these sampled volumes are denoted v1, v2;
a second series of aliquots corresponding to the sampling of several amounts of a lytic reagent R1: these sampled volumes are denoted v'1, v'2.

Each volume v'1 is adjusted so as to perform total lysis of the cells contained in each aliquot v1. The sampling valve 22 is designed so as to fluidically couple the aliquots v1 and v'1.

With reference to FIG. 6, firstly, the sampling valve 22 is positioned so as to allow the sampling of a sample in the container 27, and of the lytic reagent R1 in a container 23. These samplings are carried out by pumping using syringes 43 which also sample the buffer solution R2 in a container 24.

With reference to FIG. 7, secondly, the sampling valve 22 is positioned so as to allow the aliquots v1 and v'1 to be pushed into the measuring cuvettes 9 by the buffer solution R2, a volume v''1 of which, adjusted so as to obtain the desired final degree of dilution, is also introduced into the measuring cuvettes 9. This pushing is performed by the syringes 43.

In addition, a volume v'''1 of assay reagent R3 (specific for the protein being sought) is dispensed into the measuring cuvettes 9 by the sampling needle 21 of the immunodetection module 2.

For the assaying of an analyte such as C-reactive protein or CRP:
the lytic reagent R1 is an aqueous solution of a detergent capable of rapidly lysing the cellular elements of the sample. The detergent may be ionic or nonionic with a preference for saponin;
the buffer R2 is a buffer system capable of maintaining a pH of 8.5 in the reaction medium, for instance a glycine buffer;
the assay reagents R3 comprise a suspension of particles onto which is covalently grafted a monoclonal or polyclonal antibody capable of specifically recognizing the analyte to be assayed (in this case CRP). Optionally, a suspension may contain several populations of particles each having a different (monoclonal or polyclonal) antibody immobilized at their surface, each antibody recognizing a different epitope of the analyte to be assayed.

An example of a protocol for a range of from 2 to 200 mg/l of CRP is the following:
$v1=6.5$ µl of sample which has been prediluted in the container for measuring the white blood cells of the hematology module (1/40),
$v'1=100$ µl of saponin at 0.2% in distilled water,
$v''1=118$ µl of 0.1 M glycine buffer, pH 8.5,
$v'''1=25$ µl of a suspension of particles at 0.4%.

According to embodiment variants:
the sampling and transferring module 5 may comprise a sampling valve or a sampling system as, for example, described in document WO 2009/024710, connected to a dispensing system. It may also comprise a capillary tube instead of a needle 20;
it is possible to sample, with the second transferring means (or the transferring module) directly in one or more containers 27, one or more dilutions initially prepared for a hematological measurement. This sampling can be carried out in any container, depending on the degree of dilution and reagents used. This can also be in a container dedicated to the immunological measurement. The configuration is chosen according to two principal criteria. First of all, the mixture transferred must meet the needs of the immunological measurement (for instance the compatibility of the reagents with respect to one another, of the degrees of dilution, etc.). Next, the method must be sparingly invasive with respect to the hematological module 1, in particular, it must not substantially extend the duration of its cycle. Of course, it also must not degrade the dilutions required for the hematology module 1;
the measuring cuvette 9 may comprise a system for mixing the solution analyzed. It may be provided, without distinction, by a bubbling circuit, or by a circuit of successive suctioning and discharging in a pipe or a dedicated chamber;
the measuring cuvette 9 may not be temperature-regulated. It may comprise one or more temperature sensors used to correct the immunodetection measurements, by applying appropriate models or algorithms;

the (ultrasonic) agitation system 13 can be implemented in various ways. It may be implemented noninvasively with agitation external to the bottle, by means of dry or wet coupling between the bottle and a sonotrode. It is thus possible to use an immersed sonotrode, in the form of a vibrating needle, or even to use the sampling needle to implement the agitation;

the second transferring means 4 can be designed so as to make it possible to bring the sampling needle 21 into a container 27 of the hematology module 1. In this case, the support of the horizontal carriage 26 can be attached to the same support as the carriage 25 of the hematology module 1. It can also be attached to separate supports, optionally aligned on the axes of alignment of the cuvettes 27 of the hematology module, provided that it is aligned with the container of interest. The horizontal carriage may also be replaced with a rotary arm. In this case, the measuring cuvette 9, the rinsing cuvette 10, the bottle of particles 11 and the optional cuvette 27 of the hematological module must be aligned in an approximately circular manner about the center of rotation of this arm;

the lytic reagent R1 can be omitted in cases where the sample is first prediluted in one of the containers of the hematology module, in particular the container used for the white blood cell count. In this case, the whole blood sample can be mixed with the lytic reagent of the hematology module before being transferred into the immunodetection module. Likewise in this case, the sample receives only the buffer solution R2 and the assay reagent R3 in the immunodetection module;

the light source 30 may comprise any source of small dimension, such as a laser, a superluminescent diode, an RC-LED (resonant cavity light-emitting diode), or an incandescence lamp which is judiciously diaphragmed. It is also possible to generate the beam 32 by collimation of a light beam resulting from a single-mode optical fiber.

Figure 8:
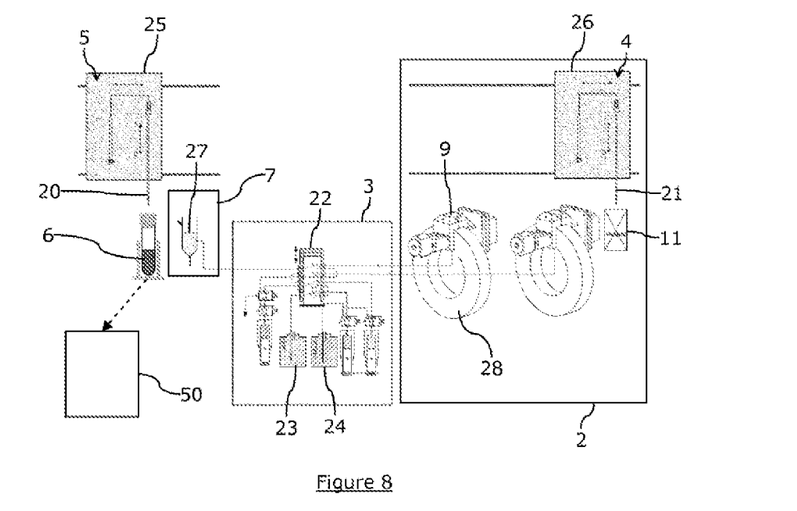
FIG. 8 presents a diagrammatic representation of a device according to the invention, according to a second embodiment.

With reference to FIG. 8, a description will now be given of a second embodiment of an analytical device for obtaining a hemogram and the assaying of at least one blood analyte using a single whole blood sample 6. This device is designed so as to make it possible to achieve a high analysis rate, of the order of at least one complete analysis per minute.

This device comprises an immunodetection module 2 and an external hematology module 50. The external hematology module 50 operates in a manner similar to the hematology module 1 of the first embodiment, and the immunodetection module 2 is identical. Thus, only the differences between the first and second embodiments will be explained in detail in what follows.

In this embodiment, it is the whole blood sample 6 which is transferred between the immunodetection module 2 and the external hematology module 50, and not, as in the first embodiment, a predilution. The hemogram measurements and measurements for assaying blood analyte(s) are therefore always carried out on the same whole blood sample 6.

The device may comprise a sample changer which makes it possible to automatically transfer the blood sample contained in a tube 6 between the immunodetection module 2 and the external hematology module 50.

The coupling of the hematology and immunodetection measurements is not limited to a sharing of the whole blood sample 6. The information is also transmitted between the modules so as to be able to use the hematology measurements to process the immunodetection measurements, as previously described. For this, the immunodetection module 2 and the external hematology module 50 may be interconnected by a computer network.

The device according to the invention always comprises first sampling and transferring means 5 and first preparing means 7 as previously described, but which are functionally attached to the immunodetection module 2. In the same way, the transferring module 3, which is identical to that of the first embodiment, is functionally attached to the immunodetection module 2.

The first preparing means 7 comprise a cuvette 27 which makes it possible to carry out a first dilution of the aliquot brought by the needle 20 from the whole blood sample 6.

The transferring module 3 comprises second transferring means with a sampling valve 22 which makes it possible to take a sample in the cuvette 27 within the first preparing means 7.

Thus, this embodiment makes it possible, as previously, to carry out immunodetection measurements with high degrees of dilution while at the same time minimizing the risks of cross-contamination between the blood sample 6 through the use of the intermediate cuvette 27.

Finally, it should be noted that the external hematology module 50 comprises its own sampling and preparing means which are separate from the first sampling and transferring means 5 and from the first preparing means 7 attached to the immunodetection module 2.

According to variants, it is possible to couple an immunodetection module 2 with several external hematology modules 50;

it is possible to couple an immunodetection module 2 with one or more external hematology module(s) 50 and a hematology module 1 as presented in the first embodiment.

Of course, the invention is not limited to the examples which have just been described, and numerous adjustments may be made to these examples without departing from the context of the invention.

The invention claimed is:

1. A method for analyzing a whole blood sample, comprising
   a) performing a hematological measurement comprising
      i) transferring the whole blood sample to one or more mixture containers;
      ii) diluting the whole blood sample with at least one lytic agent for lysing red blood cells to obtain a first diluted sample; and
      iii) obtaining at least one measurement of cell volume from said first diluted sample relative to total volume of the whole blood sample; and
   b) performing a biochemical measurement comprising
      i) transferring a portion of the first diluted sample to a preparing module, and diluting said portion of the first diluted sample with an assay reagent comprising surface functionalized particles comprising at least one ligand specific for at least one analyte of interest to obtain a second diluted sample, and binding said at least one ligand to said at least one analyte of interest; and
      ii) assaying said at least one analyte of interest by measuring, in a measuring cuvette, the degree of aggregation of said particles,
      wherein the transferring in a) and b) use different sampling needles.

2. The method of claim 1, wherein the assaying of said at least one analyte of interest comprises:

introducing into the measuring cuvette a measuring solution comprising at least one sample of said second diluted sample and said assay reagent;
measuring a first optical intensity through the measuring cuvette;
applying a magnetic field in the measuring cuvette for a given period of time, so as to allow the aggregation of said particles under the effect of the magnetic field;
after the magnetic field has been turned off, measuring a second optical intensity representative of the residual aggregation of said particles due to couplings between said at least one ligand and said at least one analyte of interest;
calculating a variation in optical density as a function of the ratio of said first and second optical intensities; and
applying a calibration function determined beforehand so as to calculate the concentration of the protein of interest from the variation in optical density.

3. The method of claim 2, wherein the second diluted sample is diluted to a degree greater than ×500 in the measuring solution.

4. The method of claim 1, wherein the lytic reagent comprises saponin.

5. The method of claim 1, comprising diluting said portion of the first diluted sample with a lytic reagent and a buffer solution capable of maintaining a defined pH to obtain a lysed sample buffer solution.

6. The method of claim 5, wherein lytic reagent comprises saponin.

7. The method of claim 1, wherein said at least one analyte of interest is C-reactive protein (CRP).

8. The method of claim 1, wherein at least one hematological and biochemical measurement are performed per minute.

9. A method for analyzing a whole blood sample, comprising
i) transferring the whole blood sample to one or more mixture containers;
ii) diluting the whole blood sample with at least one lytic agent for lysing red blood cells to obtain a first diluted sample;
iii) measuring a portion of said first diluted sample for red blood cell counts and optionally, for white blood cell and/or platelet counts;
iv) transferring a portion of the first diluted sample to a preparing module, and diluting said portion of the first diluted sample with an assay reagent comprising surface functionalized particles comprising at least one ligand specific for at least one analyte of interest to obtain a second diluted sample, and binding said at least one ligand to said at least one analyte of interest; and
v) assaying said at least one analyte of interest by measuring, in a measuring cuvette, the degree of aggregation of said particles,
wherein the transferring in i) and iii) use different sampling needles.

10. The method of claim 9, wherein the assaying of said at least one analyte of interest comprises:
introducing into the measuring cuvette a measuring solution comprising at least one sample of said second diluted sample and said assay reagent;
measuring a first optical intensity through the measuring cuvette;
applying a magnetic field in the measuring cuvette for a given period of time, so as to allow the aggregation of said particles under the effect of the magnetic field;
after the magnetic field has been turned off, measuring a second optical intensity representative of the residual aggregation of said particles due to couplings between said at least one ligand and said at least one analyte of interest;
calculating a variation in optical density as a function of the ratio of said first and second optical intensities; and
applying a calibration function determined beforehand so as to calculate the concentration of the protein of interest from the variation in optical density.

11. The method of claim 10, wherein the second diluted sample is diluted to a degree greater than ×500 in the measuring solution.

12. The method of claim 9, wherein the lytic reagent comprises saponin.

13. The method of claim 9, comprising diluting said portion of the first diluted sample with a lytic reagent and a buffer solution capable of maintaining a defined pH to obtain a lysed sample buffer solution.

14. The method of claim 13, wherein lytic reagent comprises saponin.

15. The method of claim 9, wherein said at least one analyte of interest is C-reactive protein (CRP).

16. The method of claim 9, wherein at least one hematological and biochemical measurement are performed per minute.

17. The method of claim 9, further comprising correcting the assaying step by applying the following equation:

$$OD = OD^\circ - \sum_i ai(RBC\#) \wedge i - \sum_j bi(WBC\#) \wedge j - \sum_k ci(PLT\#) \wedge k$$

where: i, j and k are integers; RBC#, WBC# and PLT# are red blood cell, white blood cell and platelet counts expressed per unit of volume (L);
OD° is the value of optical density as measured, not corrected and comprising measurement artifacts linked to an excess of cells or corresponding debris in the assaying step; and
OD is the value of the optical density corrected on the basis of data resulting from measuring red blood cell, white blood cell, and platelet counts expressed per unit of volume (L).

* * * * *